US012639852B2

(12) United States Patent　　　(10) Patent No.:　US 12,639,852 B2
Caredda et al.　　　　　　　　　　(45) Date of Patent:　　　May 26, 2026

(54) METHOD FOR PROCESSING IMAGES OF A LIVING BIOLOGICAL TISSUE WITH AUTO-CALIBRATION

(71) Applicants: UNIVERSITE CLAUDE BERNARD LYON 1, Villeurbanne (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

(72) Inventors: Charly Caredda, Villeurbanne (FR); Bruno Montcel, Lyons (FR); Michaël Sdika, Caluire (FR); Laurent Mahieu-Williame, Lyons (FR); Raphaël Sablong, Saint Martin d'Heres (FR)

(73) Assignees: UNIVERSITE CLAUDE BERNARD LYON 1, Villeurbanne (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 412 days.

(21) Appl. No.: 18/560,884

(22) PCT Filed: Apr. 12, 2022

(86) PCT No.: PCT/FR2022/050692
　　 § 371 (c)(1),
　　 (2) Date: Nov. 14, 2023

(87) PCT Pub. No.: WO2022/219284
　　 PCT Pub. Date: Oct. 20, 2022

(65) Prior Publication Data
　　 US 2024/0221221 A1　　Jul. 4, 2024

(30) Foreign Application Priority Data
　　 Apr. 13, 2021　(FR) ...................................... 2103802

(51) Int. Cl.
　　 G06T 7/80　　　　(2017.01)
　　 A61B 5/00　　　　(2006.01)
　　 (Continued)

(52) U.S. Cl.
　　 CPC .............. G06T 7/80 (2017.01); A61B 5/0077 (2013.01); G06T 7/0012 (2013.01); G06T 7/90 (2017.01);
　　 (Continued)

(58) Field of Classification Search
　　 CPC .......... G06T 7/80; G06T 7/0012; G06T 7/90; G06T 2207/10016; G06T 2207/10024;
　　 (Continued)

(56)　　　　　　References Cited

U.S. PATENT DOCUMENTS

2012/0082362 A1　　4/2012　Diem et al.
2012/0328178 A1　　12/2012　Remiszewski et al.
　　　　　　　　　　(Continued)

OTHER PUBLICATIONS

Caredda, C ("Intraoperative quantitative functional brain mapping using an RGB camera" Neurophotonics) (Year: 2019).*
　　　　　　　　　　(Continued)

*Primary Examiner* — Molly Wilburn
(74) *Attorney, Agent, or Firm* — Nixon & Vanderhye, PC

(57)　　　　　　ABSTRACT

The invention relates to a method for imaging a living biological tissue, comprising: obtaining (S1) a plurality of successive colour images of said biological tissue, the processing method comprising a calibration phase (S2) in which
　　　　　　　　　　(Continued)

at least one zonal time-dependent vector representative of the time evolution of spatial averages of intensity values of each of the colours in an area of the images is determined (S21), a bandpass filter centred on a heartbeat frequency is applied (S24), then a projection basis is determined (S26) by principal component analysis of the filtered zonal time-dependent vector, the method comprising deriving (S33) colour data representative of the time evolution of luminous intensities of the living biological tissue in the tissue images, and projecting (S35) colour data onto the projection basis.

13 Claims, 5 Drawing Sheets

(51) Int. Cl.
    *G06T 7/00*         (2017.01)
    *G06T 7/90*         (2017.01)
(52) U.S. Cl.
    CPC ................. *A61B 2560/0223* (2013.01); *G06T 2207/10016* (2013.01); *G06T 2207/10024* (2013.01); *G06T 2207/20048* (2013.01); *G06T 2207/30016* (2013.01); *G06T 2207/30104* (2013.01)

(58) Field of Classification Search
    CPC . G06T 2207/20048; G06T 2207/30016; G06T 2207/30104; G06T 2207/30004; A61B 5/0077; A61B 2560/0223
    See application file for complete search history.

(56)                References Cited

U.S. PATENT DOCUMENTS

2016/0110584 A1     4/2016   Remiszewski et al.
2019/0320875 A1*  10/2019  Jones ................... G06T 7/0012

OTHER PUBLICATIONS

Search Report for FR Application No. 2103802 dated Jan. 17, 2022, 2 pages.
International Search Report for PCT/FR2022/050692 mailed Jul. 15, 2022, 5 pages.
Written Opinion of the ISA for PCT/FR2022/050692 mailed Jul. 15, 2022, 10 pages.

\* cited by examiner (A)                                    (B)

(A)    (B)

Time (s)    Time (s)

METHOD FOR PROCESSING IMAGES OF A LIVING BIOLOGICAL TISSUE WITH AUTO-CALIBRATION

CROSS-REFERENCE TO RELATED APPLICATIONS

This application is the U.S. national phase of International Application No. PCT/FR2022/050692 filed Apr. 12, 2022 which designated the U.S. and claims priority to FR 2103802 filed Apr. 13, 2021, the entire contents of each of which are hereby incorporated by reference.

TECHNICAL FIELD

The invention relates to the field of biological imaging, and more precisely to a method for processing images of a living biological tissue.

TECHNICAL BACKGROUND

Biological imaging, generally for medical purposes, aims to highlight biological characteristics of a part of the imaged subject by image acquisition. Many biological imaging methods use complex and restrictive technologies and equipment which are only usable for one-off image acquisition that is not capable of accounting for any rapid evolution. For example, radiography or tomography uses X-rays, the dangers of which imply a large installation and a restriction on the exposure of the imaged subject. Magnetic resonance imaging requires a powerful magnetic field which can only be found inside a device excluding any magnetic object.

Thus, the use of such imaging methods is complicated for applications such as interventional imaging which requires technologies compatible with a prolonged exposure of the imaged subject and few constraints in terms of equipment, and which requires being able to report a time evolution of the imaged tissue. Interventional imaging refers to the acquisition and/or processing of data during an operation in an operating theatre.

For example, functional neuroimaging conventionally uses functional magnetic resonance imaging, fMRI, for locating functional areas of the brain. The aim of identifying functional areas is to assist the surgeon in identifying functional cortical areas associated with cognitive functions. The objective is to avoid any cognitive damage for the patient following the operation. A distance of 1 cm is generally maintained between the functional area and the resected tissue. This technique is used before, during and after the surgical operation. Preoperative fMRI enables the distance between a tumour site and a functional area to be controlled, and makes it possible, for example, to disengage the neurosurgery operation if a tumour is to close to a functional area. During the operation, the neurosurgeon performs a craniotomy (skin, cranial bone and dura matter are removed), giving the surgeon access to the patient's brain and thus access to the tumour.

The craniotomy operation involves a change in pressure of the neurocranium and a brain shift. This phenomena generates a shift in the neuronavigation points of up to 3 cm with respect to the fMRI images. It is therefore difficult to use the neuronavigation points to identify functional areas. Moreover, the size of tumours can develop drastically during the period between the fMRI acquisitions and the neurosurgical operation. This growth can introduce movement of the functional areas due to the plasticity of the brain. Although it has been possible to develop solutions enabling interventional fMRI directly incorporated in the operating theatre, many constraints remain linked to the peculiarities on this type of imaging. Electrical stimulation is therefore used systematically to identify functional areas, but this has several disadvantages. Firstly, electrical stimulation provides only low spatial precision and involves a one-off measurement, the resolution of which is defined by the distance between the anode and cathode of the stimulator. Secondly, electrical stimulation relies on the application of electrical signals to the patient's nervous system, which can cause epileptic seizures.

Other methods enabling interventional imaging typically use imagers sensitive to visible wavelengths or wavelengths close to these, such as infrared or ultra-violet, which do not entail constraints on equipment or exposure, and therefore allow imaging during the evolution of the imaged tissue over a relatively long time, for example several minutes, in an environment not dedicated to imaging, such as an operating theatre for example. Indeed, these methods can be used with compact devices suitable for the constraints of an operating theatre. Furthermore, these methods also have few risks, since they are non-invasive and non-ionising. In addition, these methods generally enable rapid data processing, which makes it possible to possess recent images very rapidly, if not in real time.

However, such methods encounter other obstacles. In particular, the living nature of the imaged tissue naturally implies variations therein over the course of the acquisition, such as variations in colours or positions for example, linked to heart pulsations or even to respiration or to voluntary or involuntary movements of the patient, which makes use of the images difficult once acquired, in particular when the images need to report characteristics such as tissue haemodynamics over periods of several tens of seconds.

Other approaches rely on detailed modelling of the propagation of light in the imaged tissue. For example, the article by Charly Caredda et al., "Intraoperative quantitative functional brain mapping using an RGB camera", Neurophoton. 6(4), 045015 (2019), doi: 10.1117/1.NPh.6.4.045015, describes an optical spectroscopy technique used for monitoring haemodynamics, which requires modelling the propagation of light. More precisely, a modified Beer-Lambert law is used, involving properties of the tissue and of the acquisition and illumination system. It is therefore a complex technique to develop, the precision of which depends on the quality of the modelling.

Some methods rely on differences in the absorption of molecules such as deoxyhaemoglobin and oxyhaemoglobin at certain wavelengths, in order to highlight certain properties of the haemodynamics based on images of the skin, as in the article by Yu Kagaya and Shimpei Miyamoto "A systematic review of near-infrared spectroscopy in flap monitoring: Current basic and clinical evidence and prospects", Journal of Plastic, Reconstructive & Aesthetic Surgery (2018) 71, 246-257, Elsevier Ltd. However, such an approach still relies on theoretical absorption models and haemodynamics, which result in the need for a statistical approach with predefined thresholds, suitable for a theoretical study but not practical for concrete use. For example, the interactions between the blood and light depend on many factors which are difficult to take into account in this manner, such as the colour of the skin or its thickness for example.

There is therefore a need for a method for imaging a living biological tissue, without the need for complex or restrictive equipment, which can highlight the evolution of the appearance of the imaged tissue during the course of the exposure, and in particular, the evolution of the colours thereof, in a simple and reliable manner, without requiring a priori knowledge of the imaged tissue via modelling.

DESCRIPTION OF THE INVENTION

A method is proposed for imaging a living biological tissue comprising obtaining a plurality of successive colour images of said biological tissue, each colour image associating intensity values of at least two colours with each of the pixels of said colour image, characterised in that the method comprises a calibration phase carried out based on a first subset of images of the plurality of colour images corresponding to one calibration period, said calibration phase comprising:

> based on images from the first subset of images, determining at least one zonal time-dependent vector representative of the time evolution of spatial averages of the intensity values of each of the colours in a zone of the images of the first subset of images,
>
> determining a characteristic frequency of a periodic physiological phenomenon based on the zonal time-dependent vector, determining a bandpass filter centred on said characteristic frequency, and the application of the bandpass filter (S24) on the zonal time-dependent vector in order to obtain a filtered zonal time-dependent vector,
>
> determining a projection basis by statistical analysis on the filtered zonal time-dependent vector, the method also being characterised in that:

> colour data, representative of the time evolution of luminous intensities of the living biological tissue in the images of the living biological tissue, are derived from a second subset of images of the plurality of successive colour images, and
>
> the colour data are projected onto the projection basis.

The proposed method uses a periodic physiological phenomenon such as heartbeats or respiratory movements in order to calibrate the use of colour data taken from colour images of the living biological tissue. It is thus then possible to highlight the haemodynamic behaviour of the imaged living biological tissue, for example in response to a stimulus, without requiring constraining imaging methods such as magnetic resonance imaging, thus allowing use in functional interventional imaging, without requiring modelling of the propagation of light in the living tissue.

The method is advantageously supplemented by the following features, taken individually or in any of the possible technical combinations thereof:

> the periodic physiological phenomenon is a heartbeat, the characteristic frequency being that of a heart pulsation, or wherein the periodic physiological phenomenon is a ventilatory movement, the characteristic frequency being that of respiration;
>
> the colour data are absorbance data representative of the time evolution of the absorbance of the living biological tissue for several colours;
>
> the absorbance data are profiles over time of variation in absorbance, representative of a variation in absorbance of each pixel over a period corresponding to the second subset of images;
>
> the variation in absorbance at an instant of a pixel is a function of a ratio between a reference intensity value for this pixel and the intensity value of this pixel at this instant;

> the plurality of successive colour images of the biological tissue comprises at least 100 images, corresponding to an acquisition frequency of at least 10 images per second, and wherein the first subset of images comprises at least 30 images;
>
> at least two colours correspond to wavelength ranges between 400 and 900 nm, and at least two colours are separated by at least 40 nm in wavelength;
>
> determining a characteristic frequency of a periodic physiological phenomenon based on the zonal time-dependent vector comprises the search for a peak of a Fourier transform modulus of the zonal time-dependent vector for each colour, and the modulus peak is searched for in a range of expected values;
>
> the bandpass filter centred on said characteristic frequency has a passband less than 0.5 Hz;
>
> the projection basis is defined by at least two principle axes resulting from the statistical analysis.

The invention also relates to an imaging system comprising an imager having a field of view in which the living biological tissue is intended to be disposed, and configured to acquire a plurality of successive colour images, and a processing unit for receiving said plurality of successive colour images, the imaging system being configured in order to implement the method according to the invention. The invention also relates to a computer program product comprising code instructions for implementing the method according to the invention when the computer reads said instructions. The computer program product preferably takes the form of a non-volatile medium readable by computer and storing program code instructions.

DESCRIPTION OF THE FIGURES

The invention will be better understood through the description below, which relates to embodiments and variants according to the present invention, given by way of non-limiting examples and explained with reference to the attached schematic drawings, in which:

FIG. 8 illustrates an application of the invention in the particular case of images of the skin of the forearm of an individual on which a tourniquet has been placed.

DETAILED DESCRIPTION

In the example used to illustrate the implementation of the invention, the imaged living biological tissue is a surface of a human brain in the context of functional neuroimaging, by way of an example of the invention. However, the invention is not limited to functional neuroimaging, and can be applied to a variety of human or animal living tissues, when the living biological tissue is subjected to a repetitive physiological variation, for example linked with heart pulsations or respiratory movements. The term "colour data" shall mean data relating to the respective luminous intensities of at least two distinct colours, in other words two distinct wavelengths or ranges of wavelengths.

In particular, the imaged living tissue can be skin, for example in the context of post-operative monitoring. Following a graft or a flap, it may be desired to check for good vascularisation of the skin by studying the haemodynamics thereof, in order to detect circulatory congestions or other anomalies. It is also possible to study the response of a tissue, such as the skin, to a stimulation such as the localised application of pressure, which is manifest by a discolouration or colouration of this skin, or exposure to a type of radiation.

It is recalled that the invention relates only to the processing of images and is therefore independent of the manner in which the images have been obtained, since they present features specific to the implementation of the invention.

Figure 1:
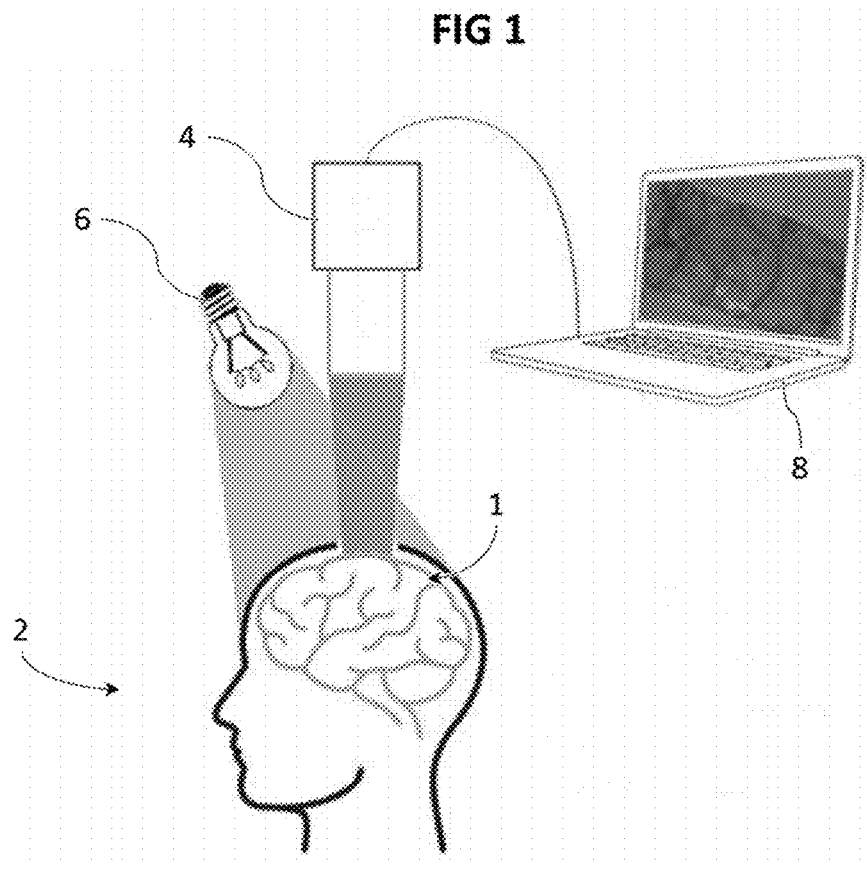
FIG. 1 is a diagram showing a simplified example of an arrangement of a system for implementing the method according to a possible embodiment of the invention.
Figure 2:
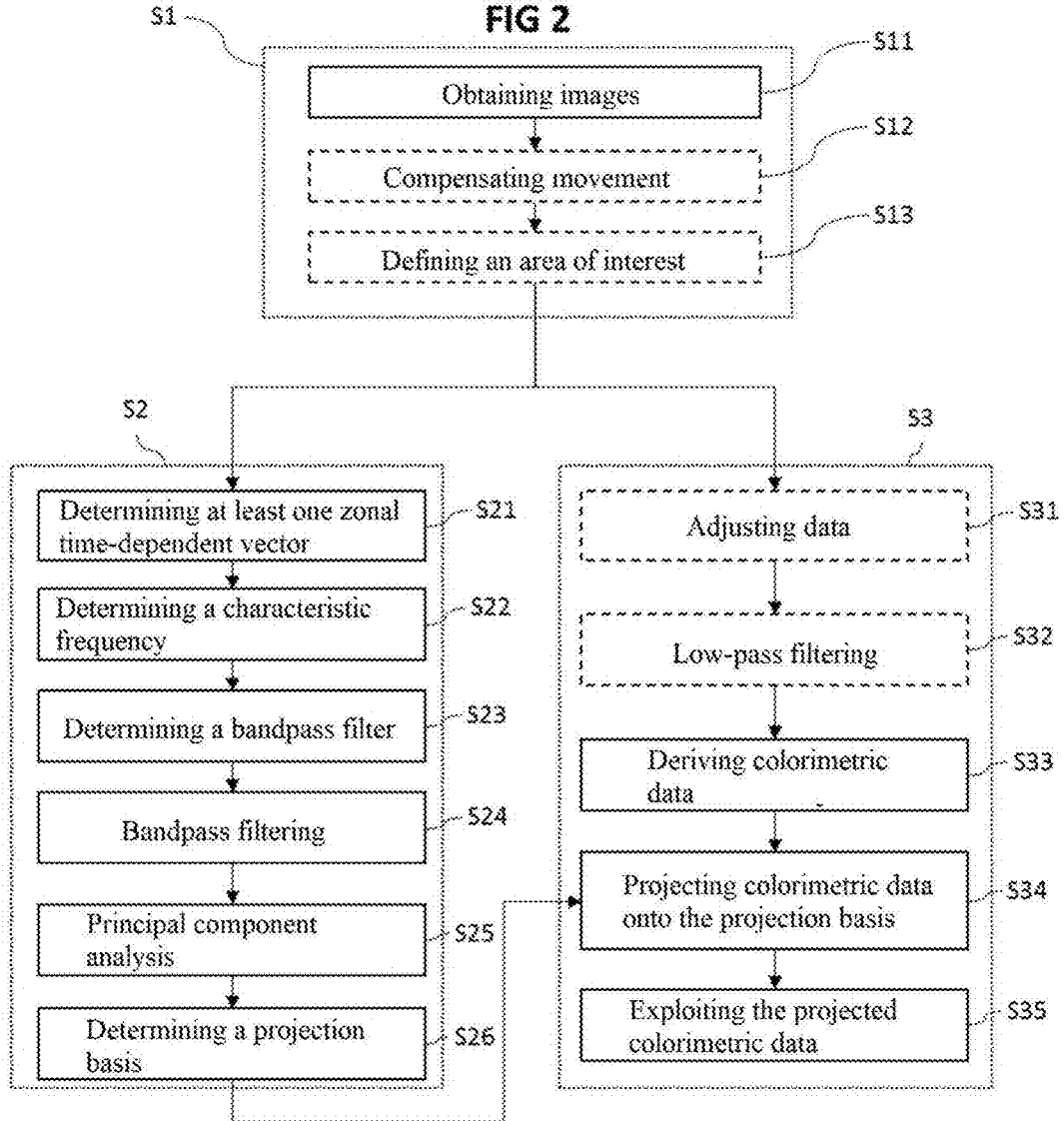
FIG. 2 is a block diagram showing steps of the method according to a possible embodiment of the invention.

With reference to FIG. 1, the imaged living biological tissue 1 in this case is a surface of a human brain of a patient 2. An imager 4 is disposed so that the imaged living tissue 1 is located in the field of view of the imager 4. The imager 4 is configured to acquire a plurality of successive colour images of said biological tissue, each colour image associating colour intensity values with each of the pixels of said colour image. The type of imager 4 is of little importance and may, for example, be a CMOS camera. The colours are typically red, green and blue, but other colours can be used, even infrared or ultraviolet. At least two colours are preferably located in the range 400-900 nm, in other words correspond to wavelength ranges between 400 and 900 nm, and preferably between 450 and 550 nm, which makes it possible to obtain a strong contrast for the haemodynamics. The resolution and frame rate are chosen to enable the evolution of the imaged living biological tissue to be reported. By way of example, it is possible to use a resolution of 1920 by 1080 pixels with a frame rate between 10 and 120 images per second, and preferably between 20 and 60 images per second. The plurality of successive colour images are acquired statically, in the sense that the living biological tissue is fixed relative to the field of view of the imager; there is no relative movement of the imager with respect to the living biological tissue, and it is therefore the same area which is imaged in the successive images. The term "colour image" shall mean a two-dimensional image, consisting of pixels spatially distributed over a surface, of intensity values of at least two colours each being associated with pixels of said colour image. By way of non-limiting example, an RGB colour image, for red-green-blue, groups pixels grouped by lines and columns, forming a two-dimensional surface, and a red intensity value, green intensity value and blue intensity value are associated with each pixel. Typically, the intensity values are at greyscale values ranging from 0 to 255. Other types of imager 4 can be used, such as a multispectral imager which acquires more than three spectral bands.

In order to improve the visibility of the imaged area of the living biological tissue, it is possible to provide a light source 6 illuminating same, for example with white light. A conventional halogen lamp can be used. It is possible to equip the light source 6 with a parabolic reflector, enabling homogeneous illumination of the cerebral cortex of the patient 1. Of course, it is possible to use all sorts of optical devices (objective lenses, filters, etc.) enabling the quality of the acquired images to be improved, which images will then be obtained by the processing unit 8. For example, crossed polarisation filters disposed on the one hand between the light source 6 and the living tissue and, on the other hand, between the living tissue and the imager 4, make it possible to limit specular reflections of the light.

The imager 4 is connected to a processing unit 8 typically in the form of a computer provided with a processor, a memory and a communication interface, to which the imager 4 transmits the acquired images. The processing unit 8 processes the images thus obtained in order to make them usable, according to the method which will be described below. The processing unit 8 can be directly connected via a connection to the imager 4, or can more broadly be capable of obtaining the images acquired by the imager 4, for example via networks such as the Internet, optionally with a temporary storage of the images acquired by the servers, in which case the processing unit 8 does not necessarily communicate with the imager 4.

The imaging method starts with obtaining (step S11), by the processing unit 8, a plurality of successive colour images of the biological tissue, for example acquired by the imager 4 or by any other means. This sequence of images comprises at least 100 images, preferably at least 300 images, and more preferably at least 600 images. The successive images cover a period of at least 10 seconds, preferably at least 30 seconds, and more preferably at least 60 seconds. The acquisition frequency is at least 10 images per second, preferably at least 20 images per second and more preferably at least 30 images per second. In the example which follows, the images are acquired over a period of 100 seconds at an acquisition frequency of 30 images per second, i.e. 3000 images in total. The images are colour images, in other words each image associates intensity values of at least two colours with each of the pixels, and preferably at least three colours. In the example that follows, the images are red-green-blue images, or RGB. Preferably, at least two distinct colours are defined by wavelengths or ranges of wavelengths separated by at least 40 nm, and preferably each colour is separated from the other colours by at least 40 nm in wavelength.

In the context of functional neuroimaging, a periodic stimulation engenders a cerebral response that is manifest by colorimetric variations at the surface of the brain, the locations of which enable the functional areas to be identified. The example which follows is a functional test of the motor functions of the hand. The patient is at rest for R seconds, in other words the studied functional areas (motor functions of the hand) are not stimulated, then the functional area for motor functions is produced for R seconds by the patient's hand movement (movement performed by the patient or by another person). More precisely, this movement is an opening and closing of the hand repeated at a frequency of approximately 1 Hz. This cycle is repeated at least twice. In this example, R is 20 seconds. Of course, the period R can be different, and the periods of rest and stimulation do not need to have the same duration. The image acquisition covers at least the two stimulation cycles.

Other periods can be chosen, in particular as a function of the nature of the imaged tissue. For example, for the skin, a longer period can be chosen when it is sought to highlight the variations in colour over a long period linked to blood irrigation of the skin, or similar periods when it is desired to highlight the response of the skin to a stimulation.

In order to improve the exploitability of the obtained images, it is possible to implement a compensation of the movement (step S12) in order to obtain a spatial correspondence between the successive images. The aim of the movement compensation is to guarantee that the light acquired for each pixel of the imager 4 corresponds to the same location of the imaged tissue throughout the image acquisition. More specifically, it is possible that the relative positions between the imager 4 and the imaged tissue are not totally stable over the course of the acquisition period. For example, the surface of the brain is subjected to a repetitive physiological movement linked to heart pulsations and respiration of the patient. Similarly, the skin can present movements which depend on the location where it is situated, for example linked to respiration or movements of the person.

The movement compensation can, for example, follow the method proposed by M. Sdika, et al., "*Robust real time motion compensation for intraoperative video processing during neurosurgery*". In 2016 IEEE 13th International Symposium on Biomedical Imaging (ISBI), pages 1046-1049, April 2016, or M. Sdika, Laure Alston, David Rousseau, Jacques Guyotat, Laurent Mahieu-Williame, and Bruno Montcel, "*Repetitive motion compensation for real time intraoperative video processing*", Medical Image Analysis, 53:1 10, 2019. The images are firstly converted into greyscale images. Each image of the video stream is offset relative to the first image acquired. The readjustment of an image acquired at time t relative to that acquired at t=0 is carried out using a deformation map determined based on several images.

It is then possible to define a subspace of each image in order to constitute a region of interest or ROI (step S13). This region of interest can be manually defined by a user on an image, which can be improved via an automatic segmentation step. The implementation of the rest of the method is restricted to this region of interest. It is possible that the region of interest covers the entire image, in which case it is not necessary to define it. However, the region of interest preferably consists substantially of an imaged area that is able to exhibit variations in colours caused by the haemodynamics of the living tissue. The definition of the region of interest therefore aims to exclude the parts of the image less susceptible to exhibiting variations in colours, for example corresponding to other parts of the body. It should be noted that the region of interest can cover a minority of the part of the image able to exhibit variations in colours, and that several regions of interest can therefore be defined. Typically, the region of interest corresponds to an area of the imaged tissue which would appear on all the images, despite any possible relative movement between the imager and the imaged tissue, which most often leads to defining a region of interest that does not cover the entire image, with sufficient margin that said region of interest is present on all the images. For reasons of simplicity, in the following the "image" will be referred to in order to designate the region of interest.

The image data resulting from this optional preprocessing are temporal colorimetric data in the form of a matrix of dimensions N×T₁×C, where N is the number of pixels contained in the image (in other words the region of interest), T₁ the number of images in the first subset and C the number of colours. In the example used, C=3, and therefore the matrix has dimensions N×T₁×3. Hence a time-dependent intensity profile is obtained for each colour.

Based on the obtained, and preferably preprocessed, images of the biological tissue, the method implements a calibration phase (step S2) carried out based on a first subset of images of the plurality of colour images corresponding to a calibration period. Since the calibration phase (S2) is implemented based on the same set of images originating from the phase where the images were obtained (step S1) as the set then used in the exploitation phase (step S3), the calibration can be qualified as auto-calibration.

The first image subset may correspond to only a part of the plurality of successive images. The calibration period preferably corresponds to a period of at least 5 seconds, and preferably at least 10 seconds, and more preferably to a period of at least 15 seconds. The first subset of images comprises at least 50 successive images, and preferably at least 100 successive images. The number of images of the first subset of images and the calibration period are chosen in order to cover the entirety of at least 5 cycles of the periodic physiological phenomenon (heartbeats or respiratory movements), and preferably at least ten cycles of the periodic physiological phenomenon. Is also possible that the first subset of images corresponds to all of the plurality of successive colour images. In this example, all the images obtained constitute the first subset of images, but it is possible to choose fewer images. In the case of functional neuroimaging, the first set of images can advantageously correspond to one or more rest periods.

The calibration phase (step S2) aims to learn the colorimetric variations linked to the periodic physiological phenomenon in the images obtained, in order to be able to highlight the variations of colours linked to blood flows that are not linked to this periodic physiological phenomenon. It is noted that the calibration does not assume any a priori knowledge of the characteristics of the imaged tissue or of those of the phenomenon to be highlighted. Thus, in order to monitor the tissue haemodynamics (for example in order to locate an area of activity of the brain, or to detect anomalies in vascularisation of the skin), it is not necessary to know the optical properties of blood or of the tissue. The calibration simply requires the presence of a periodic physiological phenomenon that is able to produce colorimetric variations similar to those that it is desired to highlight. The calibration therefore frees itself from any modelling and generalisation approximation and, being carried out during the same imaging session, is specific to each imaging session, and therefore adapted to the specific properties of each imaged living tissue.

To this effect, at least one zonal time-dependent vector representative of the time evolution of spatial averages of the intensity values of each of the colours in an area of the images of the first subset of images is determined (step S21). The vector is time-dependent in that it conserves the time dimension, and thus T1 is the number of tissue images in the first subset and the length of the zonal time-dependent vector. The area used can cover all or part of the extent of the region of interest. This area preferably extends sufficiently that the spatial average for this area erases potential inhomogeneities in colour variations. Thus, the area preferably covers at least 10% of the region of interest, and preferably at least 25% of the region of interest, and can cover all of the region of interest. In the case where the zonal time-dependent vector is derived for an area covering only a part of the region of interest, several areas can be defined and therefore several vectors can be determined, with one vector for each area. Preferably, and for the purpose of simplification, a single area covers all of the region of interest in the example described, such that the zonal time-dependent vector takes the form of a vector with dimensions $T_1 \times 3$, each value corresponds to the average over the region of interest of the intensity values of a colour in the image, corresponding to one instant.

The zonal time-dependent vector is used to identify the time-dependent variations in the luminous intensity associated with the periodic physiological phenomenon, and hence to define a bandpass filter for selecting these intensity variations (Filter Hc). For this purpose, a characteristic frequency of the periodic physiological phenomenon is determined based on the zonal time-dependent vector (step S22). This characteristic frequency is, for example, a frequency of heart pulsation when the periodic physiological phenomenon is a heartbeat, or a respiration frequency when the periodic physiological phenomenon is a ventilatory movement.

Although the characteristic frequency can be determined based on a single colour, this characteristic frequency is preferably determined based on a combination of colours, for example an average, in other words based on the part of the zonal time-dependent vector constituted of averages over the spectral dimension of the intensity values. This determination involves the Fourier transform of the zonal time-dependent vector and, more precisely, the modulus of this Fourier transformation, which can highlight the contribution of the heart pulsations on the colorimetric variations. Indeed, the fast Fourier transform is used because of the discrete nature of the values of the zonal time-dependent vector.

Figure 3:
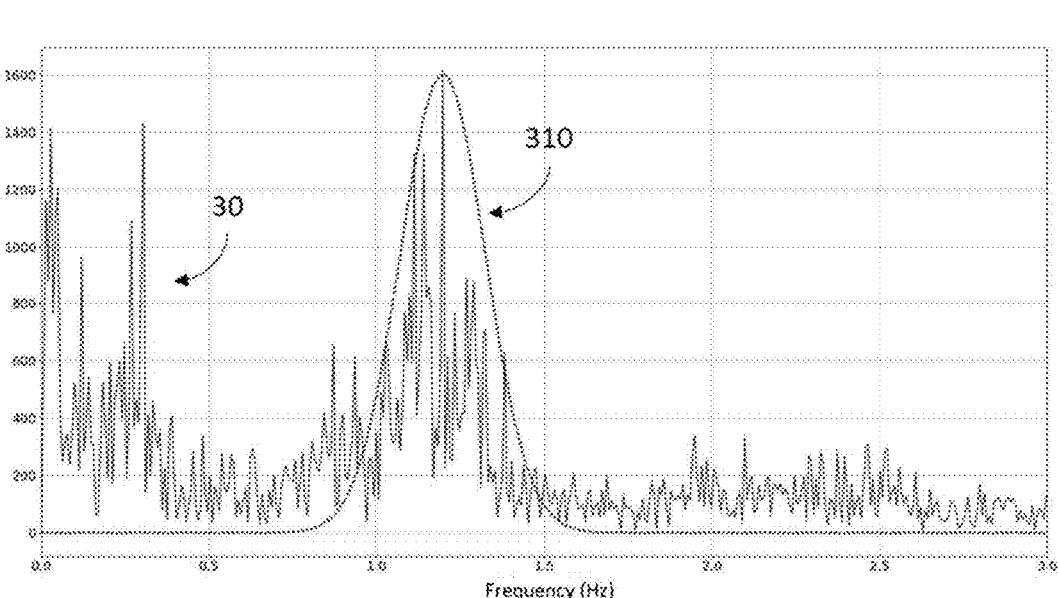
FIG. 3 shows Fourier transform moduli of components of different colours of the zonal time-dependent vector, with the window of the bandpass filter, in an exemplary embodiment of the invention.

FIG. 3 shows the modulus 30 of the fast Fourier transform of the zonal time-dependent vector consisting of averages of the intensity values of the three colours in an illustrative example where the periodic physiological phenomenon is a heartbeat. The peak of the modulus is searched for in a range of expected values. In the illustrated example where the periodic physiological function is a heartbeat, the peak of the modulus is for example searched for between 0.5 Hz and 1.5 Hz, and preferably between 0.8 Hz and 1.4 Hz. In the example of FIG. 3, the heartbeat frequency Fc is identified as being 1.19 Hz. When the periodic physiological phenomenon is a ventilatory movement for respiration, the peak of the modulus is, for example, searched for in a range between 0.1 Hz and 0.6 Hz, or even between 0.1 Hz and 0.5 Hz.

Once the peak frequency is identified, the harmonics of this peak frequency can be searched for in order to confirm the peak frequency. It is, for example, possible to construct an estimator comparing moduli of these harmonics with a threshold in order to confirm that the peak corresponds well with the characteristic frequency searched for, otherwise a secondary peak is selected. It is however not necessary to search for the harmonics, in particular if these are confused with the noise.

Once the characteristic frequency of the periodic physiological phenomenon has been determined, a bandpass filter Hc is determined (step S23). The peak frequency of the modulus, in other words the characteristic frequency, is used in order to centre the pass window defining the bandpass filter Hc. The bandpass filter Hc is thus constructed centred on the characteristic frequency, for example as a window defined by a Gaussian function with a maximum amplitude of 1, an average equal to the characteristic frequency and a width at half-height of 0.3 Hz. By way of illustration, FIG. 3 superposes a Gaussian window 31 of the bandpass filter Hc with the modulus 30 of the Fourier transform of the zonal time-dependent vector averaged over the spectral dimension with a scale multiplied by 1600 for legibility reasons. The Gaussian window 31 is centred on the previously identified cardiac frequency of 1.19 Hz.

It is possible to use other types of windows, such as a Blackmann or Hamming window, for example. The width of the window, or the passband at −3 dB, of the bandpass filter Hc is chosen to be sufficient to report a possible variation in the characteristic frequency over the course of the image acquisition, while operating effective filtering. This passband is preferably less than 0.5 Hz, and more preferably less than 0.25 Hz. During the bandpass filtering (step S24), the bandpass filter Hc is applied to the zonal time-dependent vector in order to obtain a filtered zonal time-dependent vector. More precisely, each colour component is individually filtered by the bandpass filter Hc. The filtering of the zonal time-dependent vector by the bandpass filter Hc makes it possible to isolate the colorimetric variations resulting from the periodic physiological phenomenon in order to implement a calibration based on these variations which would then enable the exploitation of the tissue images.

A statistical analysis is then carried out (step S25) on the filtered zonal time-dependent vector.

In the embodiment detailed below, this statistical analysis is a principal component analysis (PCA). The PCA enables the definition of a chromatic orthonormal projection basis (step S26) which best represents the statistical spread of the variations in luminous intensities associated with the heart pulsation. PCA is a multivariate statistical method which consists of transforming the variables that are correlated with one another into new variables that are uncorrelated with one another. These new variables are called principal components and can better explain the colorimetric inertia. Prior to the PCA, it is possible to transform the values of the filtered zonal time-dependent vector into reduced centred variables (average zero and standard deviation equal to 1). This transformation is applied in the example below.

Figure 4:
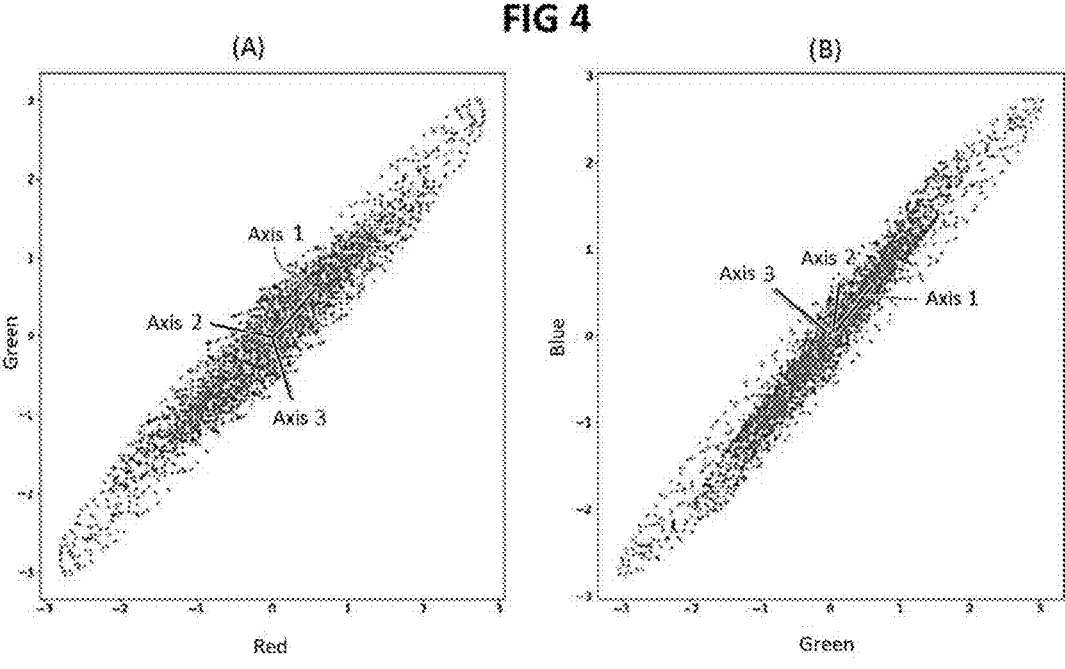
FIG. 4 shows examples of intensity values in an RGB basis, and the axes of the new projection basis.

FIG. 4 shows the spread of the used values of the filtered zonal time-dependent vector and the axes of the chromatic projection basis resulting from the PCA for the filtered zonal time-dependent vector from the example of FIG. 3. The number of axes of the chromatic projection is less than or equal to the number of colour components of the image. Preferably, at least two axes are selected. In this example with three colour components, three chromatic projection axes have been selected, but two axes could have been selected. In the case where the periodic physiological phenomenon is a heartbeat, physiological meanings can be attributed to certain axes: the first axis substantially reports the variation of blood volume in the tissue, while the second axis substantially reports the variation in oxyhaemoglobin. Indeed, the heartbeat causes a periodic variation in the blood volume, thus the total haemoglobin (first axis of the PCA), with however a mainly oxygenated transport (second axis of the PCA). However, it should be noted that this interpretation does not influence the determination of the axes of the chromatic projection basis resulting from the PCA, since these are derived statistically based on colour component values of the filtered zonal time-dependent vector.

In FIG. 4, the graph (A) on the left illustrates the pairs of values of the red (horizontal axis) and green (vertical axis) components, and the graph (B) on the right illustrates the pairs of values of the green (horizontal axis) and blue (vertical axis) components. The axes of the chromatic projection basis are represented starting from the origin of each graph. Axis 1 is the main projection axis, which expresses the vast majority of the colorimetric spread (more than 90%), while axes 2 and 3 express the spread more weakly. In the example used, the projection matrix resulting from the PCA and enabling the projection of values onto the chromatic projection basis, is:

$$B_c = \begin{bmatrix} pca_1^T \\ pca_2^T \\ pca_3^T \end{bmatrix} = \begin{bmatrix} 0,57331436 & 0,58206009 & 0,57664261 \\ -0,77296295 & 0,15082054 & 0,6162641 \\ 0,27173318 & -0,79903643 & 0,53637847 \end{bmatrix}$$

The calibration phase (S2) is achieved once the chromatic projection basis, or its equivalent the projection matrix, is determined. The tissue images can therefore be processed during an exploitation phase (step S3). More precisely, a second subset of images of the plurality of successive colour images is exploited. The second subset of images comprises the majority of the tissue images obtained, can be distinct from the first subset of images, or can comprise a part of the first subset of images. The second subset of images preferably corresponds to the totality of the tissue images obtained, or at least includes all of the first subset of images. The fact that the auto-calibration on the first subset of images is made on the data subsequently exploited in the second subset of images, enables a more robust calibration, which further makes it possible to remove any calibration delay constraints, since no time is allocated uniquely to the calibration, and does not cause loss of data, since the images used for the calibration are also subsequently exploited. In addition, the same image acquisition is carried out both for the calibration and for exploiting the images during processing of the tissue images.

As explained above, the intensity values can be expressed in the form of a matrix of dimensions $N \times T_2 \times C$, where N is the number of pixels contained in the image (in other words the region of interest), $T_2$ the number of images of the second subset of images and C the number of colours. In the example used, C=3, and therefore the matrix has dimensions $N \times T_2 \times 3$. These intensity values form a time-dependent intensity profile for each colour. However, it is not these values which are projected directly onto the chromatic projection basis. Colour data representative of the time evolution of the luminous intensity of the living biological tissue in the image are derived from the second subset of images of the plurality of successive colour images, and it is these colour data which are projected onto the chromatic projection basis.

Prior to the derivation of the colour data, the colour intensity values can undergo various optional preprocessings. A first preprocessing consists of an adjustment of the data (step S31). For each pixel from the imager 4, the measured intensity can decrease during the acquisition due to the phenomenon of desiccation of the imaged biological tissue. This is particularly the case for cortical tissue in the case of functional neuroimaging, but other biological tissues cannot undergo such drying out. During the acquisition of image data, the haemodynamic response to a physiological stimulus is measured. The image acquisition typically extends over several tens of seconds. Due to the drying out of the imaged biological tissue, a drift in intensity over time can be produced, which affects the intensity values in the tissue images. Thus, over the course of two rest periods of the patient, the luminous intensities collected will not be identical because of the time which separates them and the desiccation of the tissue during this time. This intensity drift is dependent on the angle of the incident light at the imager 4, its wavelength and the type of biological tissue. In order to correct this intensity drift for each pixel of the imager 4 and for each spectral channel (each colour), a linear regression is applied to the intensity values corresponding to the distinct rest periods in order to determine a straight-line equation D=a×t, where t designates the acquisition time and a designates the leading coefficient of the straight line. In order to improve the precision of line determination, the rest periods taken into account are preferably the longest possible, and can advantageously be the periods starting and ending the image acquisition. Then, at each intensity value of an instant t (for all periods) the drift value D of the straight line corresponding to the same instant t is subtracted for each colour.

Another possible preprocessing is the application of a low-pass filter (step S32), which, for example, can remove variations in intensity linked to phenomena exhibiting a more rapid dynamic than that which is it desired to be highlight. For example, it may involve respiration, movements of the imaged subject, or even removing haemodynamic fluctuations associated with brain activity, depending in particular on the type of tissue imaged. The type of filter, the cut-off frequency and its area of application depend on the characteristics of the processed data and the information being sought. The low-pass filter can, for example, be a Butterworth filter, Bessel filter, elliptical filter or Chebyshev filter. The low-pass filter typically has a cut-off frequency between 0.02 Hz and 0.5 Hz, preferably less than 0.25 Hz. The low-pass filter can be applied in the time domain, for example by discrete convolution of the time profile with a filter having infinite impulse response, or in the Fourier domain, for example with a Blackman filter.

Once the time profiles constituted by the intensity values have been optionally preprocessed, the colour data can be derived (step S33). Preferably, the colour data are absorbance data representative of the time evolution in the absorbance of the living biological tissue for several colours. To this effect, an absorbance variation vector $\Delta A$ is calculated for each colour time profile. Here, absorbance means the capacity of the biological tissue to absorb light passing through it. For each colour i (e.g. red, green or blue), the variation in absorbance $\Delta A$ at an instant t of a pixel is a function of a ratio between a reference intensity value for this pixel (time-independent) and the intensity value of this pixel at instant t. More precisely, the variation in absorbance $\Delta A$ is a function of the logarithm (e.g. in base 10) of this ratio. Thus, the absorbance variation vector $\Delta A_i$ for a colour i can be:

$$\Delta A_i(x, y, t) = \log_{10}\left(\frac{I_i^{Ref}(x, y)}{I_i(x, y, t)}\right)$$

with $I_i(x,y,t)$ designating the intensity value for the pixel at position (x,y) at instant t. The reference intensity value $I_i^{Ref}$ depends on the position of the pixel, but not on the time. This reference intensity value is derived from intensity values for the same pixel during a reference period, and is for example an average of these intensity values. The reference period covers several seconds and is preferably greater than seconds. The reference period preferably corresponds to a rest episode of the imaged tissue relative to that which it is desired to highlight. For example, if it is desired to highlight the haemodynamic response to a physiological stimulation, as in the case of functional neuroimaging, the period covered by the reference period corresponds to a rest period, in other words a period without stimulation. Thus, it is possible to take:

$$I_i^{Ref}(x, y) = \frac{\sum_{t=N_1}^{N_2} I_i(x, y, t)}{N_2 - N_1}$$

where $N_1$ and $N_2$ designate time indices of the start and end of the reference period. Therefore, for a pixel, an absorbance variation vector $\Delta A$ of dimension $T_2 \times C$ is obtained, where C is the number of colours, 3 in this example.

For each pixel, the absorbance variation time profiles are projected onto the chromatic projection basis (step S34), typically by matrix product of the absorbance variation vector with the projection matrix $B_c$, in order to give the projected absorbance variation time profiles, expressed by the matrix $\Delta C$: $\Delta C = B_c \times \Delta A$. In the example, the projection basis represents the three principal axes originating from the PCA, and the projection matrix $B_c$ therefore has size 3×3, with $\Delta A$ and $\Delta C$ being 3×$T_2$ matrices. It is however possible to keep only two axes, so that the projection matrix $B_c$ is of size 2×3, and $\Delta C$ is a 2×$T_2$ matrix.

Once the projected absorbance variation time profiles are obtained, these can be put in a form enabling easier exploitation, and in particular enabling better visualisation (step S35). In particular, it is possible to compare the projected absorbance variation time profiles with theoretical haemodynamic profiles. For example, the projected absorbance variation time profiles can be represented by a statistical parametric mapping, or SPM. Statistical parametric mapping of the cortical activity enables a binary indicator of the cortical activity to be defined. This representation is favoured by users because the functional areas can be directly and clearly identified in the volume of data in the form of binary information. Other approaches can be adopted according to the tissue imaged (for example, the skin), or depending on what is sought to highlight by the imaging.

Figure 5:
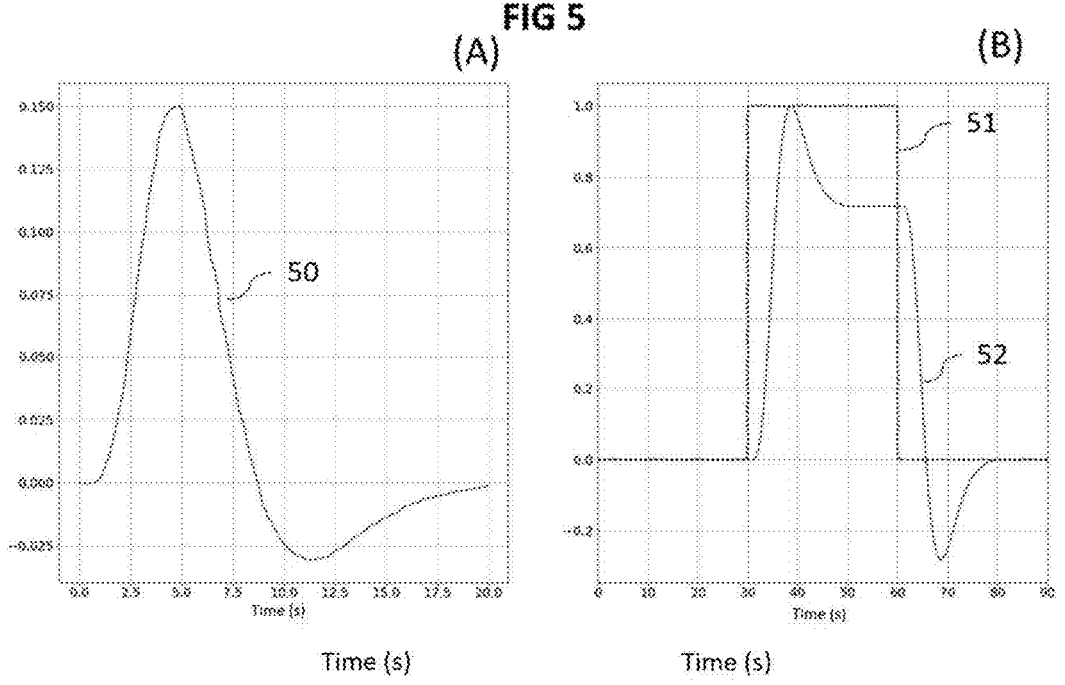
FIG. 5 shows an example of a theoretical haemodynamic impulse response and its convolution with the stimulation signal, in an exemplary embodiment of the invention.

In the example of neuroimaging, the SPM makes use of the theoretical haemodynamic response of a pixel associated with an activated functional area, which is obtained by convolution of a theoretical haemodynamic impulse response with the function representing the alternating of rest and stimulation periods (typically a rectangular function). The haemodynamic response is a physiological mechanism which consists of a local increase in the blood flow in order to meet the energy needs of active cells. The theoretical haemodynamic response can, for example, be a blood oxygen level dependent (BOLD) signal, depending on the oxygenation level of the blood, which is instead linked to the variations in deoxygenated haemoglobin. In FIG. 5, the graph (A) on the left shows an example of a theoretical haemodynamic impulse response 50 as a function of time in arbitrary units. The graph (B) on the left shows the stimulation signal 51, formed as 0 for the rest periods and 1 for the stimulation period, and the theoretical haemodynamic response 52 resulting from the convolution of the theoretical haemodynamic impulse response 50 and the stimulation signal 51.

The linear association force between the projected absorbance variation time profiles with the theoretical haemodynamic response is expressed by the general linear model, which, for example, takes the form $\Delta C = X\beta + e$, where X is a design matrix of dimensions $T_2 \times S$, with S designating the number of physiological conditions, in this case S=2 (rest and stimulation), while ß is a parameter matrix of dimensions S×N, N being the number of pixels. The parameter matrix B contains the parameters of the linear model manifesting the association for each pixel with the physiological conditions expressed in the design matrix. The error matrix e represents the errors of the model, assumed to be independent errors consisting of Gaussian noise with zero average and variance matrix $\Sigma_e = \sigma^2 \times Id$, with $\sigma^2$ the variance in the error e, and Id the identity matrix. Under these hypotheses, the parameter matrix $\beta$ can be, for example, estimated by the Gauss-Markov theorem:

$$\beta = (A^t X)^{-1} X^t \Delta C$$

where t designates the transposition operator and $(X'X)^{-1}$ the pseudo-inverse matrix de $(X'X)$ obtained by breakdown into singular values. The statistics matrix $t_{sat}$ for the test of the null hypothesis (no activation) can be:

$$t_{sat} = \frac{c^t \beta}{\sqrt{\sigma^2 c^t (X^t X)^{-1} c}}$$

where c designates the contrast vector enabling the extraction of the parameters of the matrix $\beta$ linked to one of the physiological conditions (one condition from the S conditions defined in the design matrix). For example, if two conditions have been modelled (rest and stimulation), c=[1 0] enables the parameters linked to rest to be extracted and c=[0 1] enables the parameters linked to stimulation to be extracted. The purpose of this statistics matrix $t_{sat}$ of dimensions N×1 is to calculate statistical interferences, in other words the association or otherwise of a pixel with an area considered to be active, in other words in the case of functional neuroimaging, whether the pixel is part of a stimulated cerebral functional area.

A statistical significance threshold is then defined. It is possible to use Random Field Theory. A two-dimensional image is reconstructed based on the statistics matrix $t_{sat}$ and converted into a dimension z, or score z, in other words the difference between the results and the average, divided by the standard deviation. This image of dimension z is then smoothed by convolution using a Gaussian kernel, for which the width at half height makes it possible to determine the number of resolution elements, or resel. Random field theory enables the Euler characteristic (EC) to be calculated as a function of a given statistical threshold (threshold of the smoothed z statistical image). The EC represents a property of a thresholded image. The EC corresponds to the estimation of the number of clusters (assembly of pixels) obtained after thresholding of the image at the Zth value. Random field theory stipulates that for high thresholds, the probability that EC≥1 (in other words that at least one cluster is detected) is approximately equal to E[EC] (average of EC). It is thus possible to determine thresholds which have a certain proportion of the image highlighted as containing at least one area above the threshold, in other words a cluster. For example, the Zth threshold can be determined such that the probability of identifying at least one cluster (functional area) in the statistical image z such that the null hypothesis (no activity) is rejected at 5% statistical significance. More information can be found in M. Brett, W. Penny, S. Kiebel, CHAPTER 17—Parametric procedures, Editor(s): Karl Friston, John Ashburner, Stefan Kiebel, Thomas Nichols, William Penny, Statistical Parametric Mapping, Academic Press, 2007, Pages 223-231, ISBN 9780123725608, or in J. Cao and K. J. Worsley. "Applications of Random Fields in Human Brain Mapping", pages 169-182. Springer New York, New York, NY, 2001.

The statistical parametric representations of the projected absorbance variation time profiles (for each axis, three in this example) can then be displayed. For example, the pixels associated with an activated cerebral area may appear in one colour, whereas those associated with a non-activated cerebral area appear in another colour. In order to assist the location, the statistical parametric representations of the projected absorbance variation time profiles can be superposed on an image of the living biological tissue.

Figure 6:
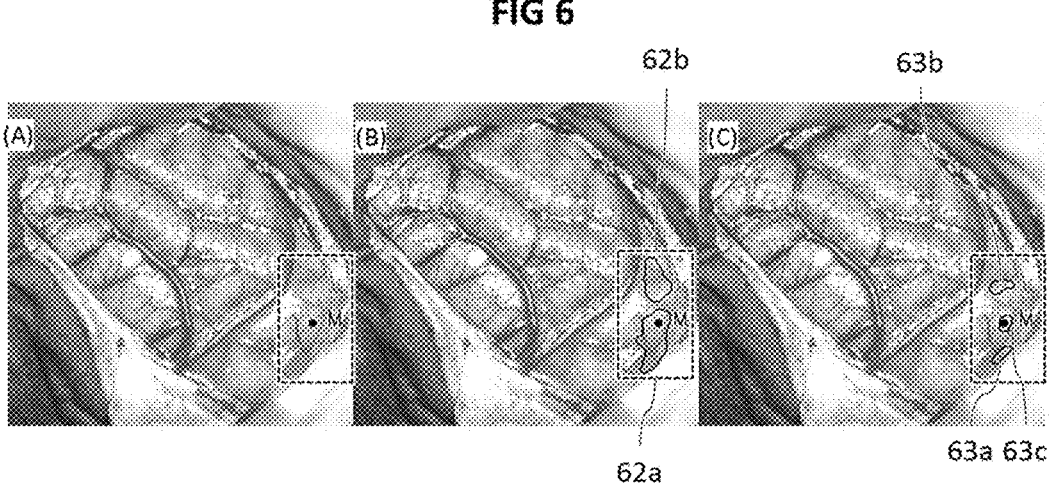
FIG. 6 shows an example of superposition of an image of the tissue with the statistical parametric representations of profiles of the variation over time in absorbance projected for various projected profiles of variation in absorbance over time, according to a possible embodiment of the invention.

For example, FIG. 6 shows an example of superposition of an image of the living biological tissue with a binary mask of statistical parametric representations of projected absorbance variation time profiles for three projected absorbance variation time profiles: the first image (A) on the left corresponds to the statistical inference of the first projected absorbance variation time profile $\Delta C1$, the second image (B), in the centre, corresponds to the statistical inference of the second projected absorbance variation time profile $\Delta C2$, the third image (C), on the right, correspond to the statistical inference of the third projected absorbance variation time profile $\Delta C3$. In each image, a dashed-line frame shows the location of the area stimulated during the periods of stimulation.

The sets of pixels associated with an activated cerebral area, highlighted by the statistical parametric representations of the projected absorbance variation time profiles, are encircled in black. By comparing the images, firstly it is observed that activated cerebral areas appear in the statistical inferences of the second and third projected absorbance variation time profiles, whereas the statistical inferences of the first projected absorbance variation time profile $\Delta C1$ do not show them. In addition, it is observed that the locations of these activated cerebral areas differ substantially, the statistical inferences of the second projected absorbance variation time profile $\Delta C2$ highlight second activated areas 62a, 62b that are more extended than the third activated areas 63a, 63b, 63c highlighted by the statistical inferences of the third projected absorbance variation time profile $\Delta C3$. Thus, the projected absorbance variation time profiles are not redundant, but can highlight diverse colorimetric variations. However, the third activated areas 63a, 63b, 63c are located in locations covered by the second activated areas 62a, 62b, which shows that the detection of these activated areas results from a similar physiological process, namely the flow of blood caused by the stimulation. Indeed, the proposed method can highlight the location of the haemodynamic response in the imaged biological tissue based on a two-dimensional colour image, through an auto-calibration phase relying on the presence of a periodic physiological phenomenon giving rise to colorimetric variations.

More specifically, the dot designated by M locates the motor area of the patient's right hand, identified beforehand by electrical stimulation. It is observed that this motor area belongs to the activated area during periods of stimulation for which the haemodynamic response is detected by the proposed method. What is more, the method can demonstrate that the cerebral area effectively mobilised for the motor functions of the right hand is more extended than the motor area identified by electrical stimulation. The method thus enables a more effective and complete identification of the functional areas of the brain in this non-limiting example.

In this example, the auto-calibration phase based on heartbeats has made it possible to define axes of representation underlining the colorimetric variations similar to those caused by these heartbeats, to which it may be possible to give a physiological interpretation.

Figure 7:
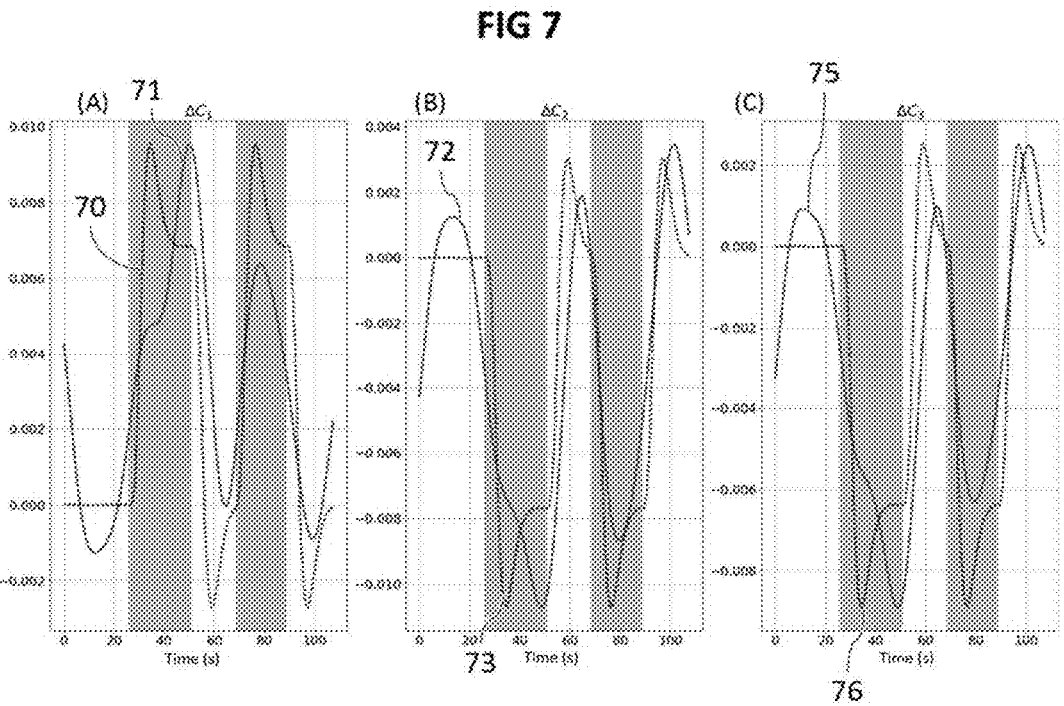
FIG. 7 shows projected profiles of variation in absorbance over time, projected onto the projection basis, combined with the theoretical haemodynamic response.
Figure 7:
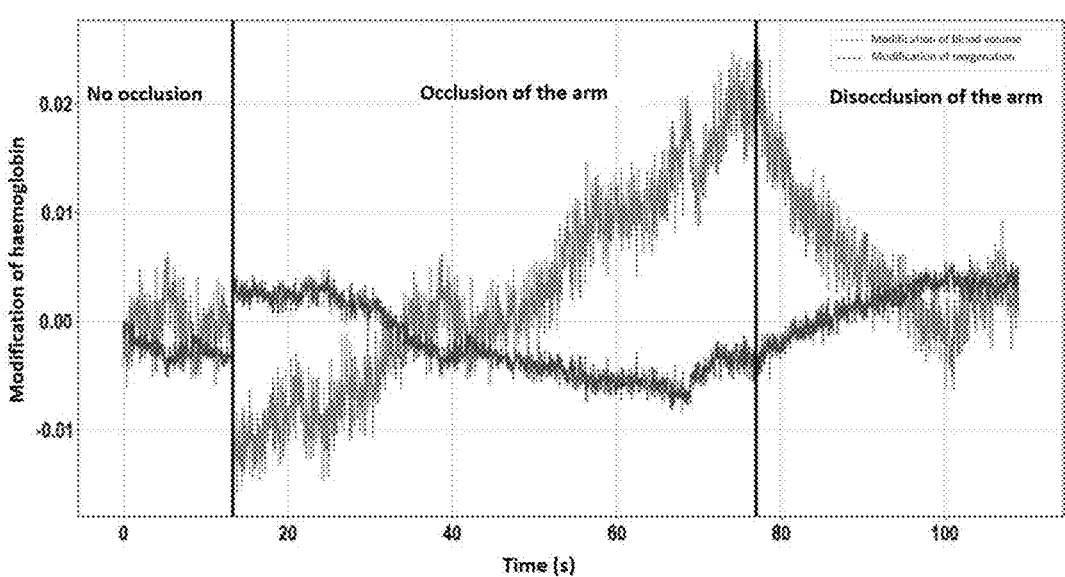

FIG. 7 shows the variation over time in the spatial averages, on the surface of the motor area for the left hand identified by electrical stimulation, of the projected absorbance variation time profiles on the projection basis. The alternating of light and dark areas illustrates the alternating of rest (light areas) and stimulation (dark areas) periods. In graph (A), on the left, curve 70 presents the first projected absorbance variation time profile $\Delta C1$, and curve 71 a theoretical haemodynamic response of the motor area corresponding to the variations in blood volume (total haemoglobin). In graph (B), in the centre, curve 72 presents the second projected absorbance variation time profile $\Delta C2$, and curve 73 the theoretical haemodynamic response of the motor area corresponding to a variation in oxyhaemoglobin. In graph (C), on the right, curve 75 presents the third projected absorbance variation time profile $\Delta C3$, and curve 76 the theoretical haemodynamic response of the motor area corresponding to a variation in oxyhaemoglobin. It can be observed in this figure, FIG. 7, that the first projected absorbance variation time profile $\Delta C1$ has similarities to the theoretical haemodynamic response corresponding to the variations in blood volume, and therefore can report the variations in blood volume based on colorimetric variations of the imaged tissue. The second projected absorbance variation time profile $\Delta C2$ and the third projected absorbance variation time profile $\Delta C3$ have strong similarities between then, and have the same variations as the theoretical haemodynamic response corresponding to a variation in oxyhaemoglobin. It is therefore possible to take account of the oxygenation of the blood, based on colorimetric variations of the imaged tissue. It is also observed that the information supplied by the second projected absorbance variation time profile $\Delta C2$ and the third projected absorbance variation time profile $\Delta C3$ can be considered as redundant, and that it will be possible to work with only two profiles.

FIG. 8 illustrates an application of the invention in the case of images of the skin of the forearm of an individual.

For this experiment, images were acquired by a BASLER acA2000-165uc colour camera, a tourniquet being placed at the elbow of the individual in order to cause occlusion and then disocclusion of the oxygenation of the forearm. An auto-calibration phase based on heartbeats has made it possible to define axes of representation underlining the colorimetric variations similar to those caused by these heartbeats, to which it is possible to give a physiological interpretation.

The curves of haemodynamic variations shown in FIG. 8 illustrate the time evolution of the spatial averages, at the surface of an area of the forearm, of the projected absorbance variation time profiles on a projection basis. Three periods are represented on this graph: a non-occlusion period (undisturbed oxygenation of the forearm), an occlusion period (oxygenation of the forearm constrained by the pressure of the tourniquet at the elbow) and a disocclusion (release of the pressure of the tourniquet, allowing a return to normal oxygenation of the forearm). The curve in light grey "Changes in blood volume" is positively correlated with the variations in blood volume (variations in total haemoglobin concentration) and the curve in dark grey "Changes in oxygenation" is negatively correlated with the variations in oxygenated haemoglobin concentration.

During the first, acquisition period, the variations in blood volume and oxygenated haemoglobin remain constant. Sudden variations in the blood volume and tissue oxygenation are observed from the start of the occlusion of the arm by the tourniquet. During the occlusion, the blood volume and the variations in oxygenated haemoglobin content increase. When the tourniquet is released, these variations drop to come back to the level of the variations measured without occlusion.

This figure effectively demonstrates that the auto-calibration technique makes it possible to monitor the haemodynamic variations during occlusion and disocclusion of an arm.

The invention is not limited to the embodiment described and shown in the attached figures. Modifications remain possible, in particular in terms of the constitution of the various technical features or by substitution of technical equivalents, without going beyond the scope of protection of the invention.

The invention claimed is:

1. A method for imaging a living biological tissue, comprising obtaining a plurality of successive colour images of said biological tissue, each colour image associating intensity values of at least two colours with each of the pixels of said colour image, characterised in that the method comprises a calibration phase carried out based on a first subset of images of the plurality of colour images corresponding to a calibration period, said calibration phase comprising:

based on images from the first subset of images, determining at least one zonal time-dependent vector representative of the time evolution of spatial averages of the intensity values of each of the colours in a zone of the images of the first subset of images, determining a characteristic frequency of a periodic physiological phenomenon based on the zonal time-dependent vector, determining a bandpass filter centred on said characteristic frequency, and applying the bandpass filter on the zonal time-dependent vector in order to obtain a filtered zonal time-dependent vector, determining a projection basis by statistical analysis on the filtered zonal time-dependent vector, the method also being characterised in that:

colour data, representative of the time evolution of luminous intensities of the living biological tissue in the images of the living biological tissue, are derived from a second subset of images of the plurality of successive colour images, and the colour data are projected onto the projection basis.

2. The method according to claim 1, wherein the periodic physiological phenomenon is a heartbeat, the characteristic frequency being that of one heart pulsation, or wherein the periodic physiological phenomenon is a ventilatory movement, the characteristic frequency being that of respiration.

3. The method according to claim 1, wherein the colour data are absorbance data representative of the time evolution in the absorbance of the living biological tissue for several colours.

4. The method according to claim 3, wherein the absorbance data are time profiles of variation in absorbance, representative of a variation in absorbance of each pixel over a period corresponding to the second subset of images.

5. The method according to claim 4, wherein the variation in absorbance of a pixel at an instant, is a function of a ratio between a reference intensity value for this pixel and the intensity of this pixel at this instant.

6. The method according to claim 1, wherein the plurality of successive colour images of the biological tissue comprises at least 100 images, corresponding to an acquisition frequency of at least 10 images per second, and wherein the first subset of images comprises at least 30 images.

7. The method according to claim 1, wherein at least two colours correspond to wavelength ranges between 400 and 900 nm, and at least two colours are separated by at least 40 nm in wavelength.

8. The method according to claim 1, wherein determining a characteristic frequency of a periodic physiological phenomenon based on the zonal time-dependent vector comprises searching for a peak of a modulus of a Fourier transform of the zonal time-dependent vector for each colour, and the modulus peak is searched for in a range of expected values.

9. The method according to claim 1, wherein the bandpass filter centred on said characteristic frequency has a passband less than 0.5 Hz.

10. The method according to claim 1, wherein the projection basis is defined by at least two principal axes resulting from the statistical analysis.

11. The method according to claim 1, wherein said statistical analysis on the filtered zonal time-dependent vector is a principal component analysis on the filtered zonal time-dependent vector.

12. An imaging system comprising an imager having a field of view in which the living biological tissue is intended to be disposed, and configured to acquire a plurality of successive colour images, and a processing unit for receiving said plurality of successive colour images, the imaging system being configured in order to implement the method according to claim 1.

13. A non-transitory computer readable medium having stored thereon instructions which, when executed by a processor, cause the processor to implement the method of claim 1.

* * * * *